United States Patent [19]

Chung et al.

[11] Patent Number: 5,665,882

[45] Date of Patent: Sep. 9, 1997

[54] PYRIDYL ETHYLATION OF LACTAMS

[75] Inventors: John Y. L. Chung, Edison; Dalian Zhao; James M. McNamara, both of Fanwood; David L. Hughes, Old Bridge, all of N.J.

[73] Assignee: Merck & Co., Inc., Rahway, N.J.

[21] Appl. No.: 702,487

[22] PCT Filed: Nov. 7, 1994

[86] PCT No.: PCT/US94/12671

§ 371 Date: Aug. 29, 1996

§ 102(e) Date: Aug. 29, 1996

[87] PCT Pub. No.: WO95/25101

PCT Pub. Date: Sep. 21, 1995

[51] Int. Cl.⁶ .................... C07D 211/76; C07D 223/10; C07D 401/06

[52] U.S. Cl. .................. 546/193; 540/531; 546/194; 546/278.4

[58] Field of Search .................... 546/193, 194, 546/278.4; 540/531

[56] References Cited

U.S. PATENT DOCUMENTS

| | | | |
|---|---|---|---|
| 4,829,079 | 5/1989 | Toja et al. | 514/425 |
| 4,933,354 | 6/1990 | Ikeguchi et al. | 514/343 |
| 5,079,301 | 1/1992 | Machado et al. | 525/154 |
| 5,281,585 | 1/1994 | Duggan et al. | 514/79 |

OTHER PUBLICATIONS

E.E. Mikhlina and M.V. Rubstov, ZH. Obshchei Khim., 1962, 32,2177–84 (CA(58) 90246).
Shapiro et al., J. Org. Chem. 1962, 27, 174–8.
Leonard et al., J. Med. Chem., 1966, 9, 140.

Primary Examiner—C. Warren Ivy
Assistant Examiner—Evelyn Huang
Attorney, Agent, or Firm—Richard S. Parr; Melvin Winokur

[57] ABSTRACT

The invention is a highly efficient synthesis for making compounds of formula:

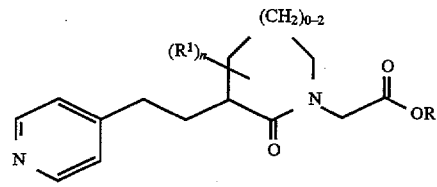

wherein n=0, 1,

R is $C_{1-4}$ alkyl or benzyl; and $R^1$, when present, is $C_{1-4}$ alkyl, OH, O—$C_{1-4}$ alkyl or S—$C_{1-4}$ alkyl. The process involves silane-mediated conjugation of 4-vinylpyridine to a substituted lactam.

10 Claims, No Drawings

PYRIDYL ETHYLATION OF LACTAMS

This application is the national phase of PCT/US94/12671 filed on Nov. 7, 1994.

BACKGROUND OF THE INVENTION

U.S. Pat. No. 5,281,585, describes fibrinogen receptor antagonists. According to the procedure described in U.S. Pat. No. 5,281,585, the compound:

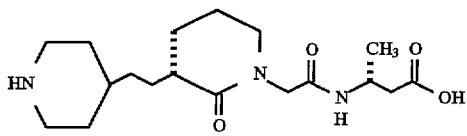

is prepared according to a 17-step procedure which requires the use of expensive reagents and numerous chromatography steps, and gives a <3% overall yield (see columns 63 to 67).

The preparation described in U.S. Pat. No. 5,281,585 involves use of 4-piperidineethanol as a starting material, and a nine step procedure leading to the intermediate

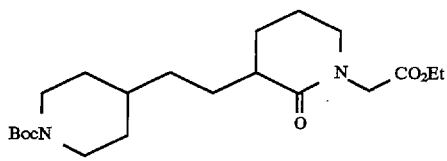

which is thereafter modified to produce various fibrinogen receptor antagonists.

According to the present invention, an important new class of compounds,

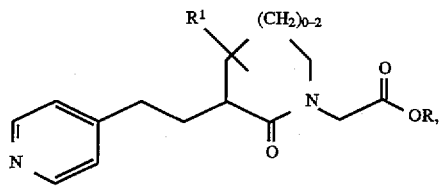

useful as intermediates for preparing numerous fibrinogen receptor antagonists described in U.S. Pat. No. 5,281,585 is prepared according to a two step process using commercially available starting materials.

SUMMARY OF THE INVENTION

The invention includes new compounds having the formula:

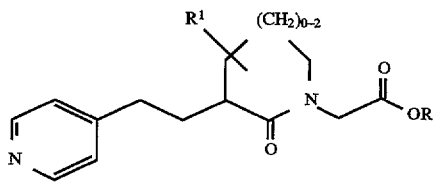

wherein
R is $C_{1-4}$ alkyl or benzyl; and
$R^1$, when present, is $C_{1-4}$ alkyl, OH, O—$C_{1-4}$ alkyl, or S—$C_{1-4}$ alkyl;

and a process for preparing these compounds, comprising a) alkylating a lactam having the formula

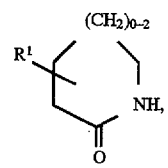 (i)

to form

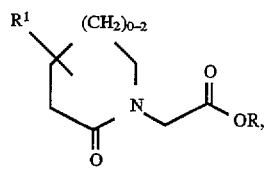 (ii)

b) dissolving the substituted lactam

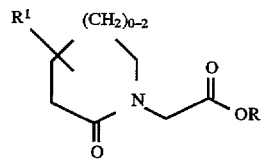 (ii)

in a non-aqueous solvent solution comprising a non-aqueous solvent and a tertiary amine base, c) dissolving a silyl derivative in the solution of (b), and
d) adding 4-vinylpyridine to the solution of (c) to form

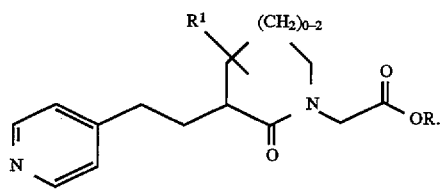 (iii)

When $R^1$ is not present, the lactam identified in i is

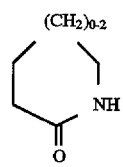

Preferably, the solution of (b) is cooled to about 0° C. and stirred for about 1–2 hours prior to addition of the silyl derivative. Also, if the silyl derivative of step c) is not an iodo silyl derivative (e.g. chlorotriethylsilane), the non-aqueous solvent system of step b) further comprises sodium iodide.

DETAILED DESCRIPTION OF THE INVENTION

The new intermediate compounds are prepared according to a process which uses a rapid, simple, and selective silyl-mediated conjugate addition of 4-vinylpyridine to a lactam.

According to the process, a lactam having the structure

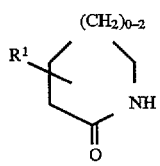

wherein

R$^1$, when present, is C$_{1-4}$ alkyl, OH, O—C$_{1-4}$ alkyl, or S—C$_{1-4}$ alkyl;
is alkylated to form

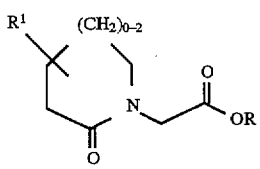

wherein

R is C$_{1-4}$ alkyl or benzyl.

4-vinylpyridine is conjugated to the substituted lactam

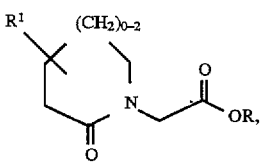

to form

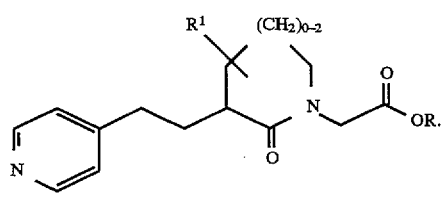

To effect conjugation, the ester ii is dissolved in a non-aqueous solvent solution, which includes a non-aqueous solvent and a tertiary amine base, and cooled to about (−10)° C. to about (+10)° C. (e.g. about 0° C.). A silyl derivative is added, at a temperature between about the cooled temperature and about 20° C., and the mixture is stirred for 1–2 hours.

If the silyl derivative is not an iodo silyl derivative (e.g. chlorotriethylsilane), the non-aqueous solvent system further comprises sodium iodide. Inclusion of sodium iodide in the non-aqueous solvent system provides in situ formation of an iodo silyl derivative.

4-vinylpyridine is then added to the resulting mixture at about (−5)° C. to about 0° C. for about 1–2 hours.

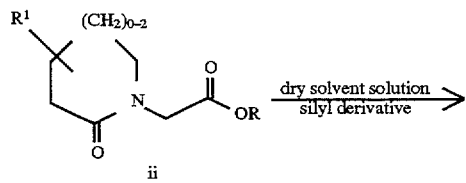

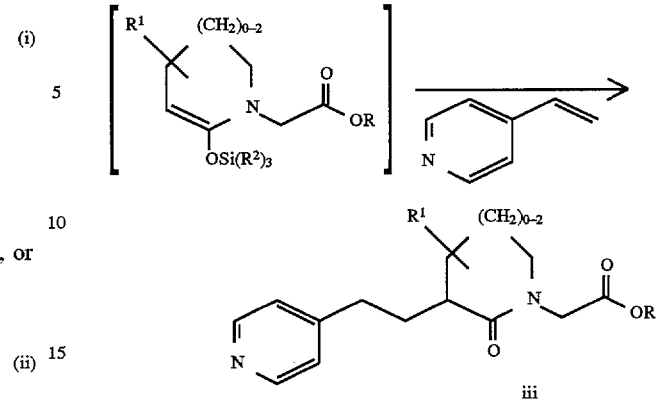

Suitable lactams useful as starting materials for the process of the present invention include 5-, 6-, and 7-membered lactams, including 2-pyrrolidinone, 2-piperidone, 2-oxohexamethyleneimine (caprolactam), all commercially available from Aldrich Chemical Co., Inc., (Milwaukee, Wis.) and substituted 2-pyrrolidinone, 2-piperidone, 2-oxohexamethyleneimine (e.g. substituted with OH, C$_{1-3}$ alkyl, or benzyl).

The suitable non-aqueous solvent solution comprises a non-aqueous solvent and a tertiary amine base. If the silyl derivative used for silyl-mediated conjugation of 4-vinylpyridine to ii is not an iodo silyl derivative, the non-aqueous solvent system further comprises sodium iodide.

Suitable non-aqueous solvents include, but are not limited to, acetonitrile, dochloromethane, toluene, diethyl ether, dipropyl ether, and t-butylmethyl ether.

Suitable tertiary amine bases include, but are not limited to, triethylamine, trimethylamine, ethyldimethylamine, and cyclic amines such as N-methyl piperidine and N-methylmorpholine.

Suitable silyl derivatives have the general formula (R$^2$)$_3$Si—X, wherein X is chloro, bromo, iodo, or —OSO$_2$CF$_3$, and wherein each R$^2$, same or different, is aryl, such as benzyl or phenyl, or C$_{1-8}$alkyl. Examples of suitable silyl derivatives include, but are not limited to, chlorotribenzylsilane, chlorotributylsilane, chlorotriethylsilane, chlorotrihexylsilane, chlorotriisobutylsilane, chlorotrimethylsilane, chlorotriphenylsilane, chlorotripropylsilane, chlorodimethylethylsilane, chlorodimethylisopropylsilane, chlorodimethyloctadecylsilane, chlorodimethyloctylsilane, chlorodimethylphenylsilane, chlorodimethylhexylsilane, bromotrimethylsilane, tertbutylchlorodimethylsilane, and iodotrimethylsilane, and triethylsilyl triflouromethanesulfonate, all commercially available from Aldrich Chemical Co., Inc., (Milwaukee, Wis.).

This process step provides an efficient and chromatography-free means for introducing the piperidinyl or pyridinyl portion of compounds described in U.S. Pat. No. 5,281,585 to the lactam portion of those compounds.

Alternatively, 4-vinyl pyridine is conjugated to a lactam, dissolved in a non-aqueous solvent system comprising a non-aqueous solvent, a tertiary base, and a silyl derivative, having the structure

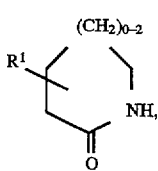

wherein $R^1$, when present, is $C_{1-4}$ alkyl, OH, O—$C_{1-4}$ alkyl, or S—$C_{1-4}$ alkyl;
to form

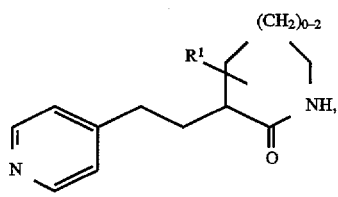

which is alkylated to form

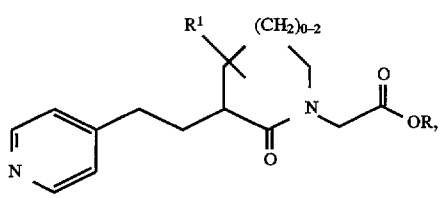

wherein R is $C_{1-4}$ alkyl or benzyl.

iii may be saponified to form

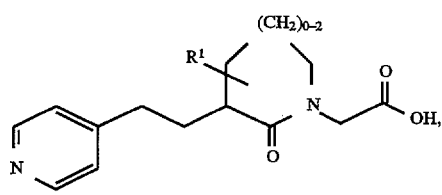

and then used to form any of a number of compounds which are useful for inhibiting the binding of fibrinogen to blood platelets. Such compounds, described in U.S. Pat. No. 5,281,585, have the general formula

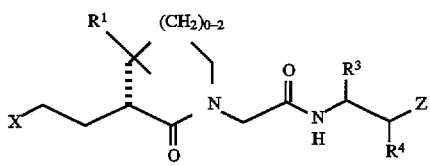

wherein X is

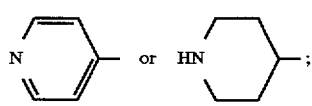

$R^3$ is hydrogen, $C_{0-6}$alkyl, either unsubstituted or substituted, with one or more groups selected from fluoro, chloro, bromo, iodo, hydroxyl, $C_{1-5}$alkylcarbonyl(CO—S alkyl)amino, aryl$C_{1-5}$ alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$ alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl ($C_{0-8}$alkyl)amino, aryl$C_{0-10}$alkyloxycarbonyl($C_{0-8}$alkyl) amino, $C_{0-8}$alkylaminocarbonyl($C_{0-8}$alkyl) amino, aryl$C_{0-8}$alkylaminocarbonyl ($C_{0-8}$ alkyl) amino, $C_{0-8}$alkylaminocarbonyloxy, aryl$C_{0-10}$alkylaminocarbonyloxy, $C_{0-8}$alkylaminosulfonyl ($C_{0-8}$alkyl)amino, aryl$C_{0-8}$alkylaminosulfonyl($C_{0-8}$alkyl) amino, $C_{0-8}$alkylaminosulfonyl, or aryl$C_{0-8}$alkylaminosulfonyl; provided that the carbon atom to which $R^3$ or $R^4$ is attached bear only one heteroatom;

$R^4$ is hydrogen, $C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$ alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl) amino, aryl $C_{0-10}$alkylsulfonyl($C_{0-8}$alkyl)amino, aryl$C_{0-8}$alkylsulfonyl, $C_{0-8}$alkylsulfonyl, hydroxycarbonyl$C_{0-5}$alkyl, $C_{1-8}$alkyloxycarbonyl ($C_{0-8}$alkyl)amino, aryl$C_{0-10}$alkyloxycarbonyl($C_{0-8}$alkyl) amino, $C_{0-8}$alkylaminocarbonyl($C_{0-8}$alkyl)amino, aryl$C_{0-8}$alkylaminocarbonyl($C_{0-8}$alkyl)amino, $C_{0-8}$alkylaminocarbonyloxy, aryl$C_{0-10}$alkylaminocarbonyloxy, $C_{0-8}$alkylaminosulfonyl- ($C_{0-8}$alkyl)amino, aryl$C_{0-8}$alkylaminosulfonyl($C_{0-8}$alkyl) amino, $C_{0-8}$alkylaminosulfonyl, or aryl$C_{0-8}$alkylaminosulfonyl; provided that the carbon atom to which $R^3$ or $R^4$ is attached bear only one heteroatom;

Z is —$CO_2R^5$,

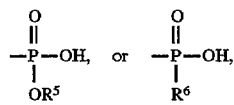

wherein $R^6$ is $C_{1-8}$alkyl, aryl, aryl$C_{1-8}$alkyl; and $R^5$ is hydrogen, $C_{1-12}$alkyl, unsubstituted or substituted, with one or more $C_{1-6}$alkyl groups,

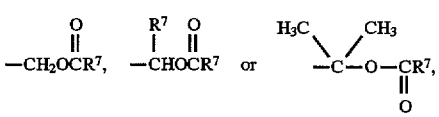

where $R^7$ is $C_{1-6}$alkyl, branched or unbranched, or phenyl, and wherein $R^7$, when appearing more than once, can be the same or different.

Hereinafter, the portion of the compound which is

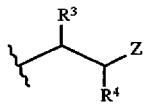

is referred to as the "amino terminal portion" of the compound.

In one embodiment of the invention, a lactam having the structure

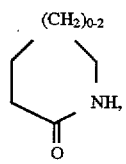  (i-1)

is alkylated to form

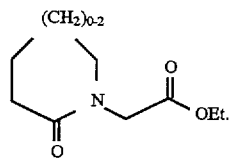  (ii-1)

4-vinylpyridine is conjugated to the substituted lactam

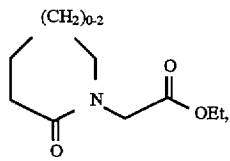  (ii-1)

to form

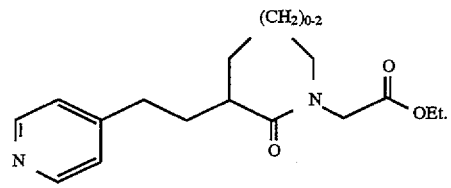  (iii-1)

In another embodiment of the invention, a lactam having the structure

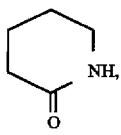  (i-2)

is alkylated to form

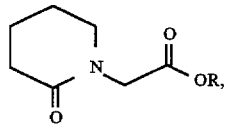  (ii-2)

wherein

R is $C_{1-4}$ alkyl or benzyl.

4-vinylpyridine is conjugated to the substituted lactam

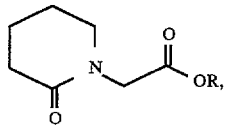  (ii-2)

to form

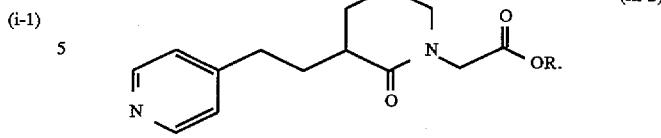  (iii-2)

In one class of the compounds which inhibit the binding of fibrinogen to blood platelets, the compounds have the formula

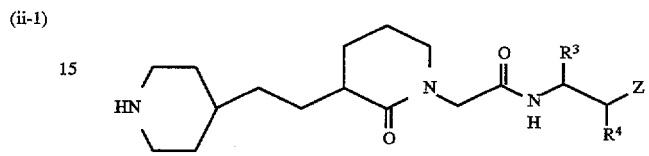

wherein $R^3$ is hydrogen, $C_{1-6}$alkyl, aryl$C_{1-6}$alkyl, or $C_{1-6}$alkyl substituted with fluoro;

$R^4$ is hydrogen; and

Z is COOH.

Exemplary compounds which may be prepared from saponified Compound iii include, but are not limited to:

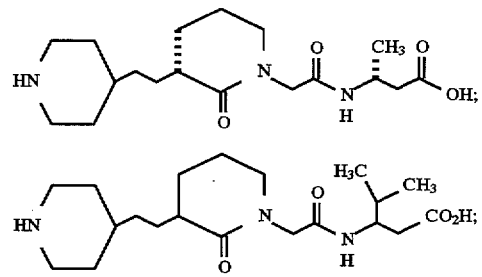

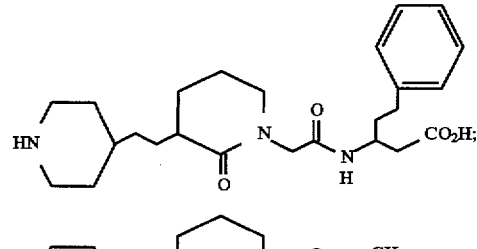

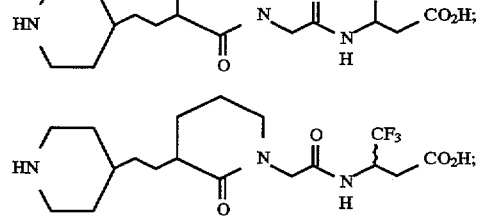

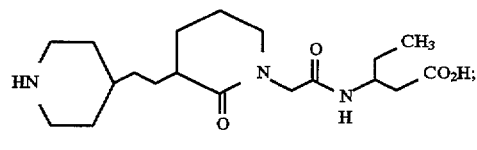

and

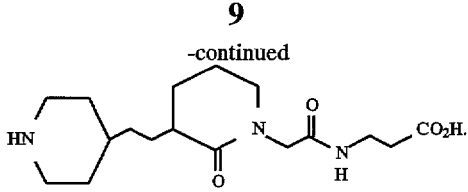

All of the above-listed compounds are active compounds as demonstrated in U.S. Pat. No. 5,281,585. The patent describes synthesis of such compounds by preparing the Boc-protected piperidinyl analog of Compound iii, which is

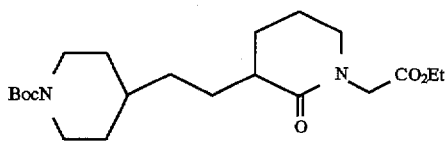

designated in column 38 as Compound 49, saponifying Compound 49, attaching the amino terminal portion according to procedures known in the art, and deprotecting the piperidinyl portion to produce the desired compound. U.S. Pat. No. 5,281,585 is hereby incorporated by reference for the purpose of identifying strategies known in the art for attaching the amino terminal portion to Compound iii or saponified Compound iii.

Fibrinogen receptor antagonists prepared with the intermediates and process of the invention may be used for inhibiting the attachment of fibrinogen to the glycoprotein IIb/IIIa receptor site. They may be administered to patients where inhibition of human or mammalian platelet aggregation or adhesion is desired.

Certain fibrinogen receptor antagonists of the invention are eliminated from circulation rapidly and are particularly useful in inhibiting platelet aggregation in situations where a strong anti-thrombotic of short duration or effectiveness is needed. Thus, these fibrinogen receptor antagonists may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

The fibrinogen receptor antagonists can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount can be employed as an anti-aggregation agent.

These fibrinogen receptor antagonists may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. The fibrinogen receptor antagonists may be administered to prevent adhesion.

Other applications include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing these fibrinogen receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of these fibrinogen receptor antagonists, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 mg/kg/minute during a constant rate infusion. Advantageously, these fibrinogen receptor antagonists may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

The fibrinogen receptor antagonists are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The fibrinogen receptor antagonists can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The fibrinogen receptor antagonists may also be delivered by the use of monoclonal antibodies as individual carriers to which the fibrinogen receptor antagonists are coupled. They may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, they may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The fibrinogen receptor antagonists can also be co-administered with suitable anticoagulation agents, including antiplatelet agents such as heparin, aspirin, warfarin, dipyridamole and other compounds and agents known to inhibit blood clot formation, or thrombolytic agents such as plasminogen activators or streptokinase, to achieve synergistic effects in the treatment of various vascular pathologies.

The activity of these fibrinogen receptor antagonists is illustrated below. One test used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with these fibrinogen receptor antagonists, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the fibrinogen receptor antagonists tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Inhibition of ADP-stimulated platelets is shown below in Table 1, which compares the concentration (dosage) of fibrinogen receptor antagonist required to inhibit aggregation by 50% relative to a control lacking the fibrinogen receptor antagonist.

TABLE 1

| Compound | $IC_{50}$ μM |
| --- | --- |
| 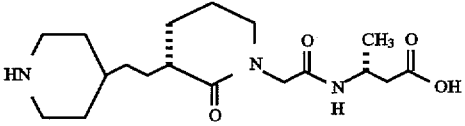 | 100 |

The following example is illustrative of the invention and should not be construed as being a limitation on the scope or spirit thereof.

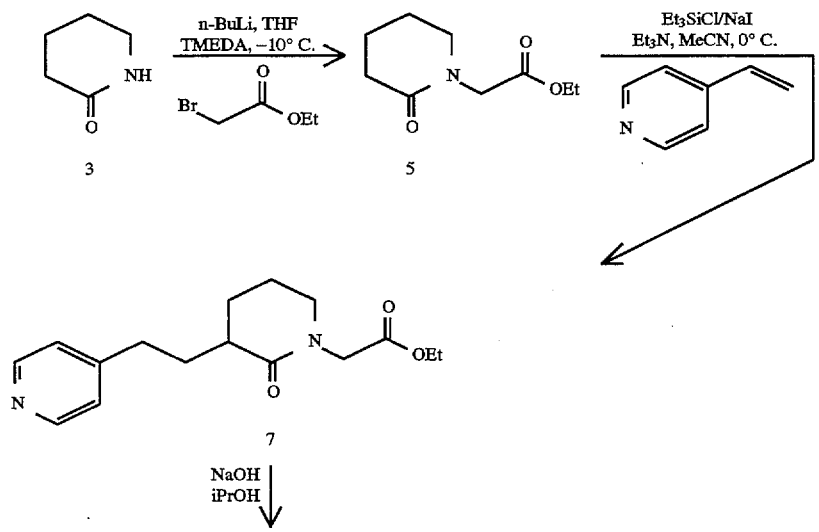

-continued

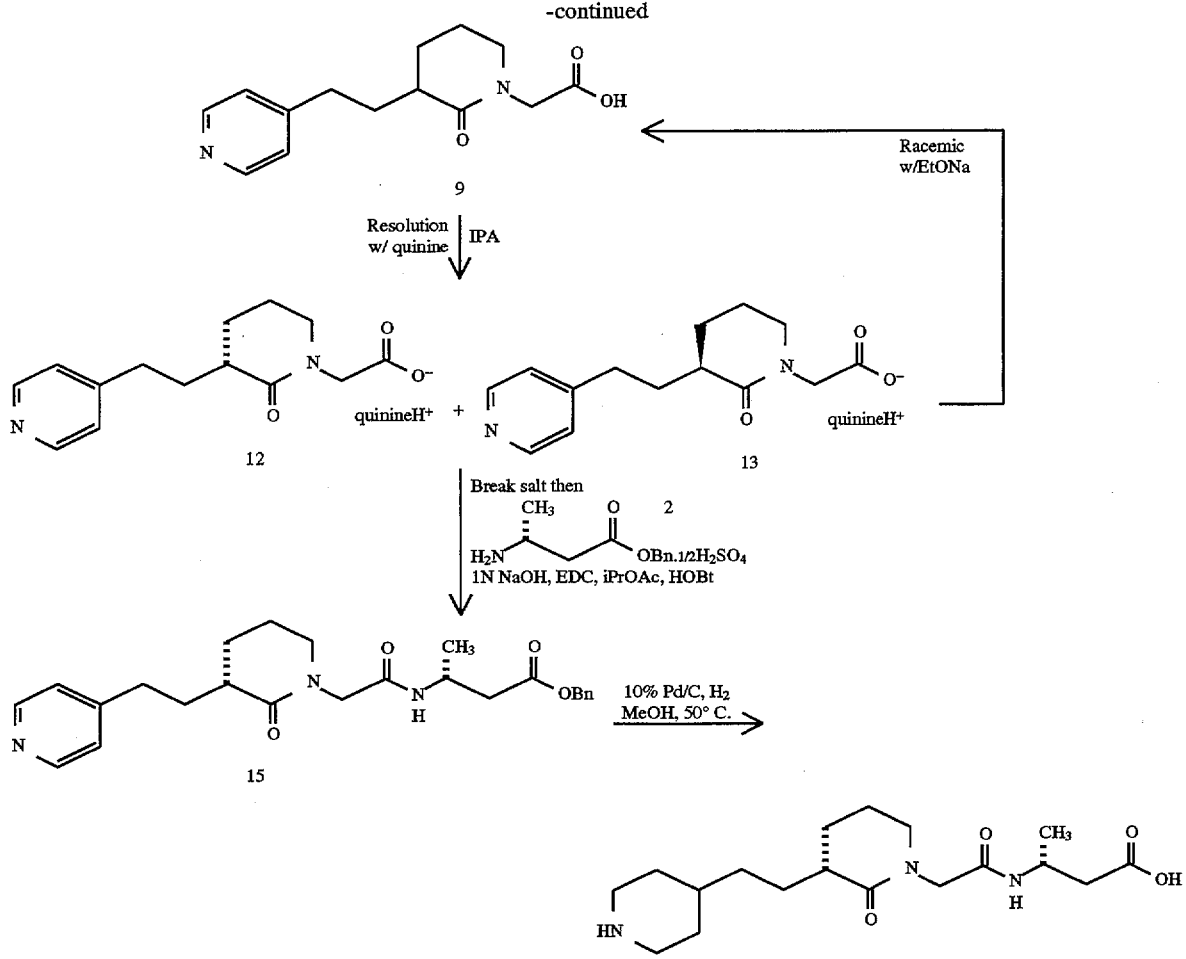

Preparation of Ethyl (2-Piperidon-1-yl)acetate (5)

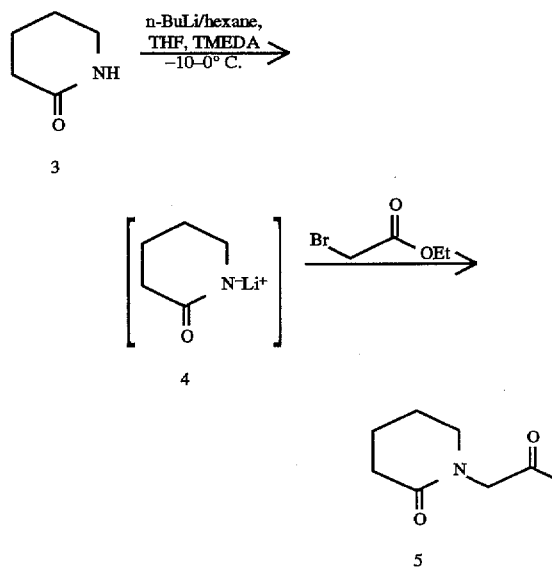

A 5 L four-necked round bottom flask was charged with 2-piperidone 3 (160.00 g, 1.614 mol), THF (1.44 L) and TMEDA (206.3 g, 1.775 mol). The mixture was stirred until all the solid dissolved, then 3 Å molecular sieves (26 g) were added. After stirring overnight, the mixture was filtered and the molecular sieves were washed with THF (0.48 L).

The combined filtrate was transferred to a dry 5 L four-necked round bottom flask equipped with a mechanical stirrer, an addition funnel, nitrogen inlet, cooling unit and a thermometer probe. The solution was cooled to −10° C. and n-butyllithium (1.6M in hexane, 1.06 L, 1.695 mol) was slowly added over a 60 min period, keeping the internal temperature less than 0° C. The mixture turned milky when ~50% of n-BuLi was charged. n-Butyllithium could be charged over 2–4 h while maintaining the internal temperature <5° C. without deterioration on the final yield. The only drawback was the slight increase in viscosity of the milky mixture.

After the addition, the reaction mixture was stirred at 0°–5° C. for 1 h. The reaction mixture was cooled to −10° C., and ethyl bromoacetate (283.1 g, 1.695 mol) was added over 15 min while maintaining the internal temperature less than 0° C. Ethyl bromoacetate could be charged over 0.5–1 h while maintaining the internal temperature <20° C. without deterioration on the final yield. The reaction mixture was stirred at 0° C. for 15 min and then allowed to warm to 23° C. and aged at this temperature for a 2 h period (or overnight if needed).

The reaction mixture was cooled to between −5° and 0° C. and quenched into a solution of NaCl (170 g) in 2N HCl (1.78 L), keeping the internal temperature less than 20° C. The resulting aqueous phase had a pH of 6.

The mixture was transferred to a 12 L separatory funnel and the two layers were separated. The aqueous layer was extracted with i-propyl acetate (3×1 L).

The combined organic layers were concentrated to near dryness and then azeotropically dried with acetonitrile (3×600 mL) (50° C., house vacuum). The mixture was filtered to remove a small amount of NaCl after the azeotropic distillation. The filter cake was washed with 500 mL acetonitrile. The combined filtrate was assayed to contained 235.4 g of product (78% yield; 83–85 area % purity at 215 nm) as a 36 wt % solution (total weight =654 g). It has a KF of 60 mg/mL and contained <2 mol % of THF and IPAC by NMR. The brown solution was used as is in the next step. Pure solid product was isolated by crystallization from isopropyl acetate/hexane.

mp: 70°–71 ° C.

$^1$HNMR (CDCl$_3$, 250 MHz) δ: 1.27 (t, J=7.1 Hz, 3 H), 1.85 (br m, 4 H), 2.42 (br m, 2 H), 3.35 (br m, 2 H), 4.10 (s, 2 H), 4.19 (q, J=7.1 Hz, 2 H).

$^{13}$C NMR (CDCl$_3$, 63 mHz) δ: 14.1, 21.3, 23.1, 32.1, 48.6, 49.2, 61.1, 169.1, 170.4.

Preparation of Ethyl [(±)3-[2-(Pyridin-4-yl)ethyl]-2-piperidon-1-yl]acetate (7)

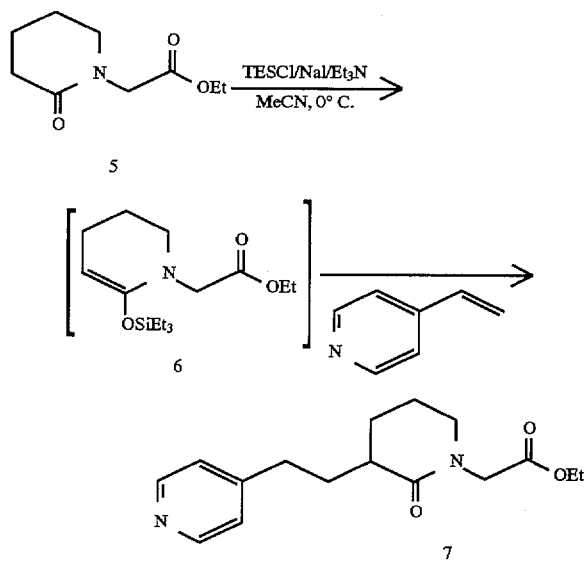

A 250 mL three-necked round bottom flask equipped with a stirrer, nitrogen inlet, cooling unit and a thermometer probe was charged with piperidone-ester5 (55.6 g, 108.0 mmol; 36 wt %; from step 1), acetonitrile (63.0 mL), anhydrous sodium iodide (17.81 g, 118.8 mmol) and triethylamine (13.11 g, 129.6 mmol). The mixture was stirred until all the solid dissolved.

The solution was cooled to 0° C. and chlorotriethylsilane (17.91 g, 19.94 mmol) was added over 5 min, keeping the internal temperature below +5° C., and then stirred at 20° C. for 1–2 h.

The resulting mixture was cooled to −5°–0° C., and 4-vinylpyridine (13.09 g, 124.2 mmol) was added dropwise over a 2 h period, while keeping the internal temperature below 0° C. The reaction was aged at 0° C. for 1–2 h, then quenched by slow addition (10 minutes) into a cold (0° C.) solution of 1N HCl (140 mL), while keeping the internal temperature <20° C. The final pH was 1.5–2.5.

The acidic solution (pH ~2) was extracted with 50% IPAC/Hexane (2×160 mL). Piperidone-ester 5 (5–7%), triethylsiloxane and residual neutral species were removed during the extractions. About 0.3% product was lost to the organic layer. At pH 3, the loss was 3%.

The aqueous layer was assayed showing 24 g of product (76% yield), 1.2 g 5 (6%) and 4.7 g of bis-pyridyl impurity 8 (11%).

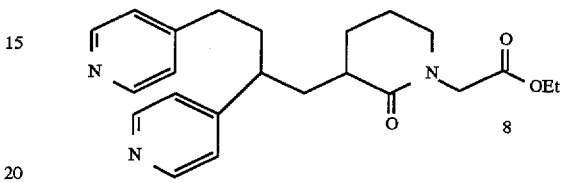

To the aqueous solution was added IPAC (1×120 mL) and the mixture was cooled to 5°–10° C. With vigorous stirring, it was then basified to pH 9.5–10 by the slow addition of solid sodium bicarbonate (10 g; to pH 6) and 5N NaOH (~22 mL; to pH 9.7). The layers were separated.

The aqueous solution was extracted with toluene (2×150 mL). About 0.1% product remained in the aqueous layer after the extractions.

The combined organic layers were washed with saturated aqueous sodium bicarbonate (3×50 mL). Three washes were required to remove 95+% of Et$_3$N.HI/NaI. Less than 0.5% of product was lost to the bicarbonate washes. The resulting organics has a total volume of 460 mL and a KF of 5.1 mg/mL.

The organic layer was azeotropically dried by distillation at 60° C. under reduce pressure. After 450 mL distilled out (final KF=<100 mg/mL), distillation was terminated and 150 mL dry toluene (total volume=200 mL) and 12 g of silica (60–200 mesh) were added. After stirring for 1 h, the mixture was filtered and the filter cake was washed with 100 mL toluene. Significant amounts of colored, polar, gummy impurities were removed by the silica treatment.

The combined filtrate was assayed to contain 21.3 g (68% overall yield; 91.8% recovery) of product 7. It was concentrated in vacuo (50° C., 100 mBar). After distilling most of the solvent, the batch was flushed with IPA (3×100 mL) to give a final concentration of 25 wt % (86 g) in IPA. This solution was used as is in the next step.

MS(EI) m/z 290 (M$^+$).

$^1$H NMR (CDCl$_3$) δ 1.09 (t, J=7.1 Hz, 3H), 1.50 (m, 1H), 1.60–1.90 (m, 2H), 2.04 (m, 1H), 2.20 (m, 1H), 2.54 (m, 2H), 3.10–3.30 (m, 2H), 3.77 (A of AB, J=17.2 Hz, 1H), 4.01 (q, J=7.1 Hz, 2H), 4.03 (B of AB, J=17.2 Hz, 1H), 6.99 (d, J=6.0 Hz, 2H), 8.30 (d, K=6.0 Hz, 2H).

$^{13}$C NMR (CDCl$_3$) δ 9.7, 17.3, 22.2, 27.9, 28.0, 36.2, 44.6, 44.9, 56.6, 119.5, 145.2, 146.6, 164.7, 168.2.

Pure product is an oil (purified by flash chromatography).

17

Preparation of [(±)3-[2-(Pyridin-4-yl)ethyl]-2-piperidon-1-yl]acetatic acid (9)

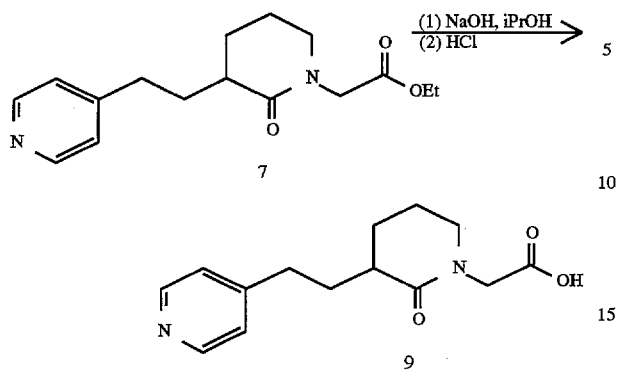

To a 25 wt % solution of the pyridine-ethyl ester 7 (21.3 g, 73.35 mmol) in isopropyl alcohol was added 48.8% aqueous sodium hydroxide (7.82 g, 95.36 mmol) at 20° C. under nitrogen over a 5 min period.

The reaction mixture was stirred for 2 h until complete consumption of 7 was observed as monitored by HPLC.

The mixture was cooled to 5–10° C., seeded with 50 mg of NaCl and then quenched by the slow addition of 36.6% aqueous hydrochloric acid (9.50 g, 95.36 mmol) over a 10 min period, while maintaining the internal temperature <15° C. The final pH was 5.45.

To the resulting mixture was added MeOH (20 mL), THF (40 mL) and Solka-Floc (5 g). After stirring for 30 min at ambient temperature, the mixture was filtered through a pad of Solka-Floc (5 g, wetted with 10 mL IPA) in a 150 mL sintered glass funnel (10–15 mm).

The filter cake was washed with a mixture of IPA/THF/MeOH (50 mL:20 mL:10 mL). Filtration of the wash took about 3 min.

The combined filtrate contained acid 9 in quantitative yield as determined by HPLC analysis.

The filtrate was dried by azeotropic distillation under vacuum at 50° C. After distilling most of the solvents, the mixture was flushed several times with IPA (3×50 mL) to give a final concentration of 30 wt % (final weight=60 g) and a KF of <1000 mg/mL.

The mixture was seeded with 9 and stirred until a seed bed was formed. Hexane (20 g, 30.5 mL) was then added over a 1 h period and then aged for 12 h. After cooling to 10° C. and stirring for 0.5 h, the solid was collected by filtration through a sintered glass funnel. The filter cake was washed with 40:60 IPA:hexanes (50 mL) and vacuum-dried under a stream of nitrogen to give 18.3 g of 9 as a light beige crystalline solid. The purity was 96.6 wt %. Thus the yield was 91.8% (17.7 g) from 7 or an overall yield of 62% from 5 for the two steps.

mp 144°–145° C.

MS(EI) m/z 263 (MH+).

$^1$H NMR (CDCl$_3$) δ 1.70 (m, 1H), 1.80–2.05 (m, 4H), 2.20 (m, 1H), 2.40 (m, 1H), 2.78 (t, J=8.0 Hz, 2H), 3.35 (m, 1H), 3.47 (m, 1H), 3.90 (A of AB, J=17.1 Hz, 1H), 4.32 (B of AB, J=17.1 Hz, 1H), 7.27 (d, J=6.2 Hz, 2H), 8.49 (d, J=6.0 Hz, 2H).

18

$^{13}$C NMR (CDCl$_3$) δ 17.4, 22.4, 28.1, 28.4, 36.3, 44.9, 45.1, 120.4, 142.7, 149.8, 167.7, 168.3.

Anal. Calcd for $C_{14}H_{18}O_3N_2$:

C, 64.1 i; H, 6.92; N, 10.68.

Found: C, 64.15; H, 7.16; N, 10.66.

Preparation of Quininium [3 (R)-(−)-[2-(Pyridin-4-yl)ethyl]-2-piperidon-1-yl]acetate (12) via Resolution of [(±)3-[2-(Pyridin-4-yl)ethyl]-2-piperidon-1-yl]acetic Acid (9) with Quinine Resolution—Salt Formation and Crystallization

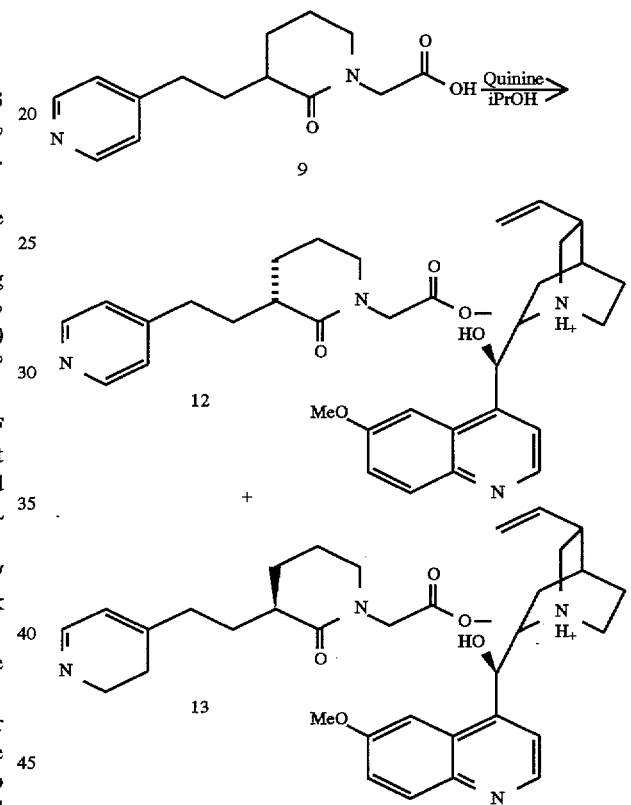

In a 250 mL round bottom flask, pyridine acid 9 (12.04 g, 96.6% pure, 44.34 mmol), quinine (14.89 g, 45.90 mmol) and isopropyl alcohol (80.8 mL; KF <0.1 mg/mL) were combined. The mixture was heated at 65° C. for 15 min under a nitrogen atmosphere to dissolve all the solid. The resulting solution was allowed to cool to 20° C. When the solution reached 45° C., it was seeded with ~10 mg of 99.5% ee quinine salt 12. After stirring overnight, the mixture was cooled to 5°–6° C. and aged for 0.5–1 h.

The solid was collected on a medium porosity fritted funnel under a nitrogen blanket. The filter cake was washed with 50 mL cold (5°–10° C.) THF:hexane (50:50) and then dried under vacuum with a nitrogen sweep to give 12.72 g of 12 as a white solid. The weight % of the free acid was 42.2%, thus the yield of free acid was 46.1% based on 44.34 mmol of 9. The optical purity of the free acid was 98% ee.

Racemization and Resolution of the Resolution Mother Liquor Preparation of Quininium [3(R)-(–)-[2-(Pyridin-4-yl)ethyl]-2-piperidon-1-yl]acetate (12)

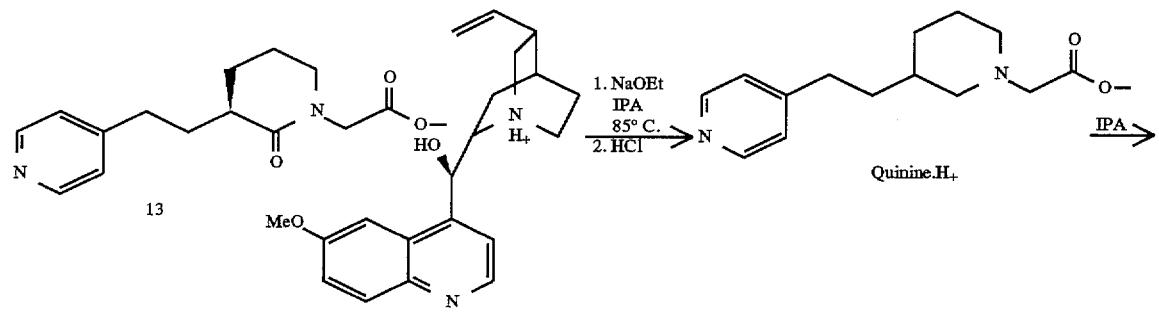

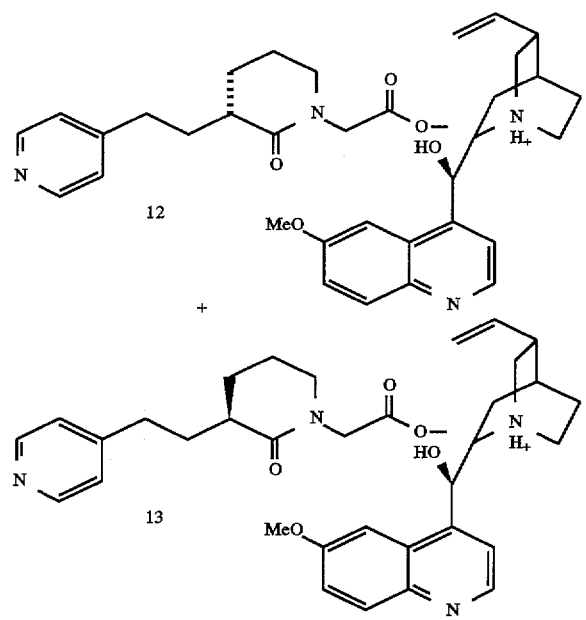

A three-necked 3 L round bottom flask equipped with a mechanical stirrer, condenser, nitrogen gas inlet and thermometer probe was charged with pyridine acid quinine salt mother liqour from the resolution step (1.84 L, 77.7 g/L, 545 mmol) and solid sodium ethoxide (67 g, 981 mmol).

The mixture was heated at reflux (83°–85° C.) for 5 h.

The resulting mixture was cooled to 15° C. and 37% hydrochloric acid (56 mL) was slowly added until pH 8.1–8.3 (at 23° C.).

To the batch was added THF (184 L) and Solka-Floc (80 g). After stirring for 1 h, the mixture was filtered through a layer of Solka-Floc (40 g, prewetted with THF) in a sintered glass funnel (medium porosity) to remove NaCl and then washed with THF (300 mL).

The filtrate was concentrated under vacuum at 45° C. and flushed with toluene (3×300 mL) to remove water, followed by isopropyl alcohol (3×300 mL) to remove toluene. The KF of the mixture should be less than 500 mg/mL after the flushes. Isopropyl alcohol (750 mL) was added to the batch to give a final concentration of 3 mL IPA per gram of quinine salt.

The mixture was heated at 70°–75° C. for 15–30 min under a nitrogen atmosphere to dissolve all the solid. The resulting solution was allowed to cool gradually to ambient. When the batch temperature reached 45° C., the mixture was seeded with 0.1 g of 99.5% ee quinine salt 12.

After stirring overnight at 22° C., the mixture was cooled to 5°–10° C. and aged for 0.5 h. The batch was filtered through a sintered glass funnel (medium porosity) and the wet cake was washed with cold hexane/THF ( 1:1, 10° C., 2×350 mL) and then dried under vacuum under a nitrogen blanket.

114–132 g of solid (32–37% yield) was obtained with ~89.5 wt % purity (9 wt % IPA, 1 wt % NaCl) and 98+%ee.

Preparation of [3 (R)-(–)-[2-(Pyridin-4-yl)ethyl]-2-piperidon-1-yl]acetyl-3-(R)-methyl-b-alanine benzyl ester (15)

Salt Breaking

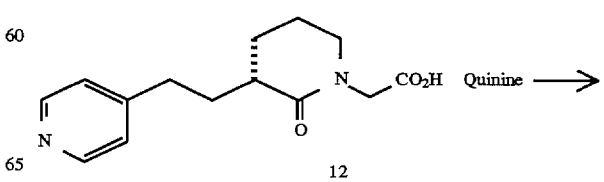

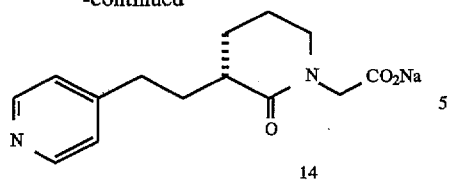

In a three-necked flask charged with 37 L isopropyl acetate was added 6711 g pyridine acid quinine salt 12. To this stirred suspension was added 10.1 L 1N sodium hydroxide slowly. The final pH of the aqueous solution was 9.5. After separation of two layers, the aqueous layer was extracted with 8.5 L isopropyl acetate. The pH of the aqueous layer was adjusted to 10.4 with 245 mL 1N sodium hydroxide and extracted with another 1.4 L isopropyl acetate.

Peptide Coupling

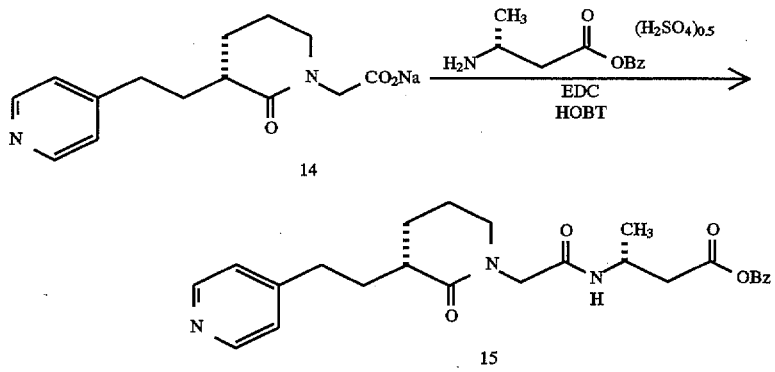

To the stirred solution of pyridine acid sodium salt 14 (10.2 mol) from the last step was added benzyl 3(R) aminobutyrate hemisulfate (2500 g, 10.3 mol), isopropyl acetate (10.2 L), HOBT (103.2 g, 0.76 mol) and 1-(3-dimethylaminopropyl)-3-ethyl carbodiimide hydrochloride (2346 g, 12.2 mol). The mixture was stirred at room temperature overnight.

After the reaction was complete, the reaction mixture was diluted with 10.2 L isopropyl acetate and the two layers were separated. The aqueous layer was extracted with another 10.2 L isopropyl acetate. The combined organic layers was washed with 10 L saturated sodium bicarbonate solution and then with 2×20 L water. The combined organic solution was used directly in the next reaction.

Alternative salt-breaking procedure using MTBE:

Preparation of [3(R)-(−)-[2-(Pyridin-4-yl)ethyl]-2-piperidon-1-yl]acetyl-3-(R)-methyl-b-alanine benzyl ester (15)

Salt Breaking

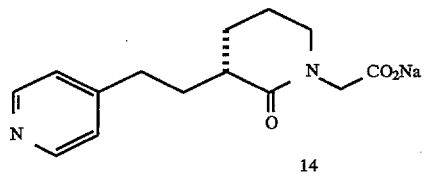

To a three-necked flask charged with 140 mL MTBE and 7.5 mL water was added 10 g of pyridine acid quinine salt 12. To this stirred suspension was added 7.5 mL 2N sodium hydroxide slowly. The final pH of the aqueous solution should be controlled to <12. After separation of two layers, the aqueous layer was extracted with 45 mL MTBE.

Peptide Coupling

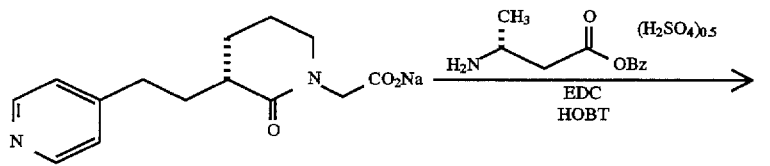

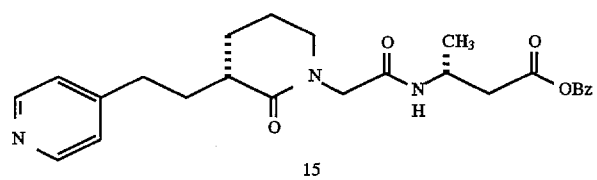

The pH of the aqueous solution of pyridine acid sodium salt 14 (14 mmol) from the last step was adjust with 1N HCl if necessary to 9–11.5. To this stirred solution of pyridine acid sodium salt was added benzyl 3(R) aminobutyrate hemisulfate (3.48 g, 14.36 mmol), isopropyl acetate (59 mL), HOBT (0.14 g, 1 mmol) and EDC (3.29 g, 17.16 mmol). The mixture was stirred at room temperature for 2–3 hrs until all the pyridine acid was consumed as judged by HPLC.

After the reaction was complete, the two layers were separated. The aqueous layer was extracted with another 14.7 mL isopropyl acetate. The combined organic layers was washed with 15 mL 5% sodium bicarbonate solution and then with 2×30 mL water. The combined organic solution was used directly for the next reaction.

Preparation of [3 (R)-(−)-[2-(Pyridin-4-yl)ethyl]-2-piperidon-1-yl]acetyl-3-(R)-methyl-β-alanine

Reduction-Deprotection

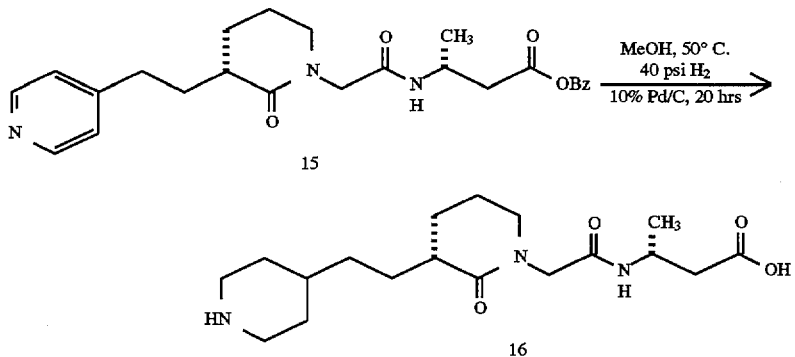

The pyridine amide benzyl ester 15 solution in isopropyl acetate from last step was concentrated under vacuum (−40° C. pot temperature) to a volume of 8 L and then 10 L methanol was added and the solution concentrated again to 8 L (KF<500 mg/mL). The methanol flush (temperature ≦50° C., 10 cm Hg) was repeated four times until all the isopropyl acetate was replaced with methanol (maximum IPAC content=50 mol % relative to benzyl ester). The resulting solution was divided into two equal portions and each subjected to the following hydrogenation condition.

To an 5-gallon stirred autoclave was added the pyridine amide benzyl ester (2231 g, 5.1 mol) solution in methanol (total volume was adjusted to 17.6 L) and 27.5 mL acetic acid. To this solution was added 211.5 g 10% Pd/C. The mixture was heated to 50° C. and hydrogenated at 40 psi for 20 h.

After the mixture was cooled to room temperature, it was filtered through ca. 5 inches thick Solka-Floc (1 kg dried in vacuum oven, pre-washed with 4×2 L methanol) and the solid was washed with 2×2.5 L methanol.

After the filtrate that contained 16 was removed, water was added to wet and recover the catalyst. The assayed amount of 16 was 3325 g (MW 353, 9.4 mol, 92% from pyridine acid quinine salt).

The filtrate was concentrated under vacuum and the total volume was adjusted to 15.3 L (12 L MeOH+3325 g 16).

This solution was heated to reflux under nitrogen and 20 L acetonitrile was added while the solution was at reflux. The solution was seeded with 0.6 g of 16 and another 5 L acetonitrile was added. The mixture was then stirred for 1 h without heating during which time the temperature dropped from 61° C. to 52° C.

Mother 25 L acetonitrile (KF=200 mcg/ml) was added slowly (30 min) without heating during which time the temperature dropped from 52° C. to 37° C.

The mixture was stirred at room temperature overnight and then filtered (KF=1.51 mg/mL). The solid was washed with 6 L acetonitrile. The solid was dried in vacuo (50° C., 10 cm Hg) overnight to give 2976 g of 16 as a white, fluffy solid (MW 353, 8.4 mol, 82.7% yield based on pyridine acid quinine salt).

What is claimed is:

1. A process for preparing compounds of the following formula:

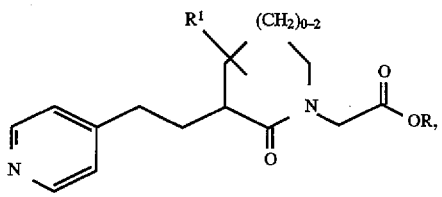

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl;

comprising a) alkylating a lactam having the formula

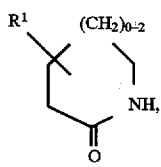

to form

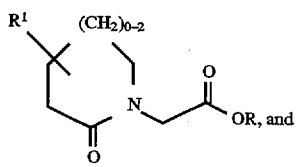

b) dissolving the substituted lactam

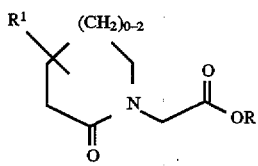

in a non-aqueous solvent solution, c) dissolving a silyl derivative in the solution of b), and d) adding 4-vinylpyridine to the solution of c) to form

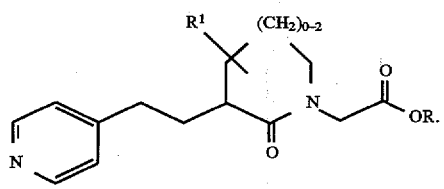

2. A process of claim 1 wherein R is ethyl and $R^1$ is not present.

3. A process according to claim 2, wherein the solution of b) comprises a non-aqueous solvent and a tertiary amine base.

4. A process according to claim 3, wherein the solution of b) is cooled to about (−10)° C. to about (+10)° C.

5. A process according to claim 4, wherein the solution of c) is stirred for about 1–2 hours.

6. A process according to claim 5, wherein the solution of c) is cooled to about (−5)° C. to about 0° C.

7. A compound having the structure

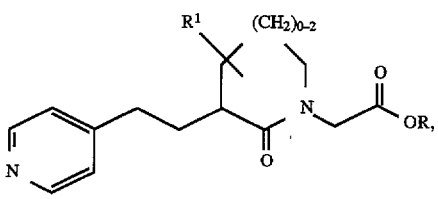

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl.

8. A compound which is

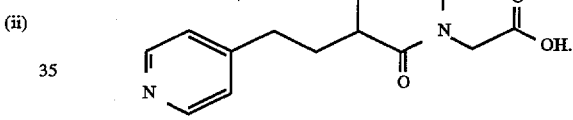

9. A compound of claim 7 which is

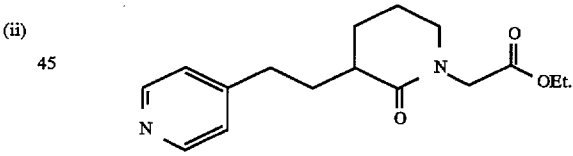

10. A process for preparing a compound of the invention which comprises a) dissolving a lactam having the structure

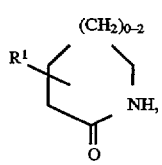

wherein $R^1$, when present, is $C_{1-4}$ alkyl, OH, O—$C_{1-4}$ alkyl, or S—$C_{1-4}$ alkyl, in a non-aqueous solvent system comprising a non-aqueous solvent, a tertiary base, and a silyl derivative,
b) conjugating 4-vinyl pyridine to the lactam to form
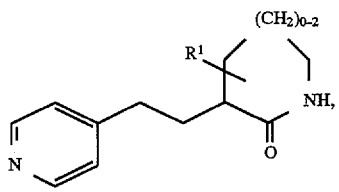
(ii-a)
c) alkylating ii-a to form
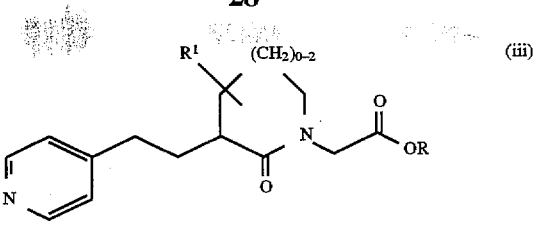
(iii)
wherein
R is $C_{1-4}$ alkyl or benzyl.
* * * * *